(12) United States Patent
Koike et al.

(10) Patent No.: US 9,101,660 B2
(45) Date of Patent: Aug. 11, 2015

(54) SOLID PREPARATION

(75) Inventors: Masahiko Koike, Osaka (JP); Hiroyoshi Koyama, Osaka (JP); Naoru Hamaguchi, Osaka (JP)

(73) Assignee: Takeda Pharmaceutical Company, Osaka (JP)

( * ) Notice: Subject to any disclaimer, the term of this patent is extended or adjusted under 35 U.S.C. 154(b) by 1204 days.

(21) Appl. No.: 10/530,262

(22) PCT Filed: Oct. 6, 2003

(86) PCT No.: PCT/JP03/12781
§ 371 (c)(1),
(2), (4) Date: Apr. 5, 2005

(87) PCT Pub. No.: WO2004/030700
PCT Pub. Date: Apr. 15, 2004

(65) Prior Publication Data
US 2005/0287207 A1    Dec. 29, 2005

(30) Foreign Application Priority Data

Oct. 7, 2002  (JP) ................................. 2002-294045

(51) Int. Cl.
| | |
|---|---|
| *A61K 31/155* | (2006.01) |
| *A61K 31/427* | (2006.01) |
| *A61K 45/06* | (2006.01) |
| *A61K 9/20* | (2006.01) |
| *A61K 9/30* | (2006.01) |
| *A61P 3/10* | (2006.01) |
| *A61K 9/28* | (2006.01) |

(52) U.S. Cl.
CPC ............... *A61K 45/06* (2013.01); *A61K 9/2027* (2013.01); *A61K 9/2054* (2013.01); *A61K 9/2059* (2013.01); *A61K 9/2866* (2013.01); *A61K 31/155* (2013.01); *A61K 31/427* (2013.01)

(58) Field of Classification Search
CPC ... A61K 31/155; A61K 31/427; A61K 45/06; A61K 31/425
USPC .......................................................... 424/464
See application file for complete search history.

(56) References Cited

U.S. PATENT DOCUMENTS

| | | | |
|---|---|---|---|
| 5,501,861 A | 3/1996 | Makino et al. | |
| 5,720,974 A | 2/1998 | Makino et al. | |
| 6,117,451 A * | 9/2000 | Kumar | 424/465 |
| 6,153,632 A | 11/2000 | Rieveley | |
| 6,287,596 B1 | 9/2001 | Murakami et al. | |
| 6,291,495 B1 | 9/2001 | Rieveley | |
| 6,403,121 B1 | 6/2002 | Adjei et al. | |
| 6,524,621 B2 | 2/2003 | Adjei et al. | |
| 2002/0004515 A1 | 1/2002 | Smith | |

FOREIGN PATENT DOCUMENTS

| | | |
|---|---|---|
| CA | 2179584 | 12/1996 |
| CA | 2294582 | 12/1998 |
| CA | 2388846 | 5/2001 |
| EP | 0 553 777 A2 | 8/1993 |
| EP | 0 749 751 | 12/1996 |
| EP | 0 861 666 A2 | 9/1998 |
| EP | 1 329 217 A1 | 7/2003 |
| JP | 05-271054 A | 10/1993 |
| JP | 11-060476 A | 3/1999 |
| JP | 2000-264836 A | 9/2000 |
| JP | 2001-335469 A | 12/2001 |
| JP | 2002-087965 A | 3/2002 |
| WO | WO 98/57634 | 12/1998 |
| WO | WO 99/03477 A1 | 1/1999 |
| WO | WO 99/47128 | 9/1999 |
| WO | WO 00/06126 A1 | 2/2000 |
| WO | WO 00/28989 | 5/2000 |
| WO | WO 00/38666 A1 | 7/2000 |
| WO | WO 00/66102 A2 | 11/2000 |
| WO | WO 01/21159 A2 | 3/2001 |
| WO | WO 01/32158 A2 | 5/2001 |
| WO | WO 01/35940 | 5/2001 |
| WO | WO 01/35941 | 5/2001 |
| WO | WO 01/82875 | 11/2001 |
| WO | WO 02/04024 | 1/2002 |
| WO | WO 02/11721 A1 | 2/2002 |
| WO | WO 02/30400 | 4/2002 |
| WO | WO 02/45693 A1 | 6/2002 |
| WO | WO 2004/006921 | 1/2004 |

OTHER PUBLICATIONS

"Remington: The Science and Practice of Pharmacy," 21st Edition, Ed. David Troy, Lippincott William & Wilkins, 2003, pp. 675-676.*
Remington's Pharmaceutical Sciences, 18th Edition, 1990, pp. 1639.*
RxList: The Internet Drug List, http://www.rxlist.com/actos-drug.htm, Accessed Jan. 27, 2009.*
Chilcott et al., "A Systematic Review of the Clinical Effectiveness of Pioglitazone in the Treatment of Type 2 Diabetes Mellitus," Clinical Therapeutics, 2001, 23(11):1792-1823.
Einhorn et al., "Pioglitazone Hydrochloride in Combination with Metformin in the Treatment of Type 2 Diabeter Mellitus: A Randomized, Placebo-Controlled Study," Clinical Therapeutics, 2000, 22(12):1395-1409.
Zhuang et al., Practical Pharmaceutical Preparation Technology, People's Medical Publishing House, Jan. 1999, p. 203-204 (and English translation thereof).
M. Suzuki, et al., "Effects of Combined Pioglitazone and Metformin on Diabetes and Obesity in Wistar Fatty Rats", *Clinical and Experimental Pharmacology and Physiology*, (2002) vol. 29, No. 4, pp. 269-274.

(Continued)

*Primary Examiner* — Rachael E Bredefeld
(74) *Attorney, Agent, or Firm* — Foley & Lardner LLP

(57) ABSTRACT

The present invention provides a solid preparation containing an insulin sensitizer and an active ingredient (except insulin sensitizers), which is useful as a therapeutic drug for diabetes and the like, and which is superior in preparation characteristics such as content uniformity and dissolution property of the insulin sensitizer and the active ingredient (except insulin sensitizers), preparation hardness and the like.

16 Claims, No Drawings

(56) References Cited

OTHER PUBLICATIONS

Shin. Yakuzaigaku Soron (Kaitei Dai 3 Han), "Introduction to Modern Pharmaceutics", *Nankodo Co., Ltd.*, (1987), pp. 155-160.
Office Action dated Jun. 17, 2008, received in corresponding Japanese Patent Application No. 2003-346699 (4 pgs.) and English translation (5 pgs.).
Office Action dated Feb. 18, 2009, in corresponding patent application in Kazakhstan, 3 pages, with English translation, 3 pages.
V.I. Chueshov. Kharkov., "Osnova", UkrFA Publishers, 1999, 370-371, 373-374.
Supplementary European Search Report dated Jun. 9, 2009, in corresponding EP 03751344, 9 pages.
"Farmacja stosowana (Pharmacy applied)," a manual for students of pharmacy, Janicki et al., Eds., Wydawnictwo PZWL, Warszawa, 2000, p. 28 (1.3 Micronization of powders), p. 204 (10.7.3 Determination of the uniformity of content of the therapeutic substance), and p. 210 (10.7.7 Determination of mechanical strength), with English translations.
Third Party Observation to corresponding EP 03751344.7, Feb. 22, 2013.
Pharmaceutical Dosage Forms: Tablets, vol. 1, $2^{nd}$ Edition, 1989, pp. 5-6, Lieberman et al., Eds.
Third Party Observation to corresponding EP 03751344.7, Mar. 27, 2013, transmittal to applicant dated Apr. 9, 2013.
Third Party Observation to corresponding EP 03751344.7, Mar. 18, 2013, transmittal to applicant dated Mar. 26, 2013.
Horiba Scientific, A Guidebook to Particle Size Analysis, 2012, 32 pages.
Opposition to EP 1561472 B1 by Generics (UK) Limited dated Jul. 10, 2014, 27 pages.
Pharmaceutical Dosage Forms and Drug Delivery Systems, 1999, Seventh edition, p. 66.
The Merck Index, Merck & Co., Inc., 2001, $13^{th}$ Edition, 1061, 1335.
Remington, The Science and Practice of Pharmacy, $20^{th}$ Edition, 2000, 656.
Opposition to EP 1561472 B1 by Dr. Klusmann dated Jul. 11, 2014, 18 pages.
Kitamori et al., "Evaluation of changes in drug particle size during tableting by measurement of dissolution of disintegrated tablets," J. Pharm. Pharmacol., 1979, 31:501-504.

\* cited by examiner

SOLID PREPARATION

This application is the National Phase filing of International Patent Application No. PCT/JP03/012781, filed Oct. 6, 2003.

TECHNICAL FIELD

The present invention relates to a solid preparation comprising an insulin sensitizer and an active ingredient (except insulin sensitizers), which is useful as a therapeutic drug for diabetes and the like.

BACKGROUND ART

There are the following reports on preparations containing an insulin sensitizer such as a thiazolidinedione and the like and an active ingredient (except insulin sensitizers).

1) A pharmaceutical agent containing an insulin sensitizer in combination with at least one member from an α-glucosidase inhibitor, an aldose reductase inhibitor, a biguanide, a statin compound, a squalene synthetase inhibitor, a fibrate compound, an LDL catabolism enhancer and an angiotensin converting enzyme inhibitor (EP749751A).
2) A pharmaceutical composition containing an insulin sensitizer, a biguanide antihyperglycaemic agent and a pharmaceutically acceptable carrier (WO98/57634, US2002/0004515A).
3) A pharmaceutical composition containing a thiazolidinedione, metformin hydrochloride and a pharmaceutically acceptable carrier, wherein the thiazolidinedione is formulated upon the surface of metformin hydrochloride (WO01/35940).
4) A pharmaceutical composition containing a thiazolidinedione, metformin hydrochloride and a pharmaceutically acceptable carrier, wherein the thiazolidinedione and metformin hydrochloride are respectively dispersed in pharmaceutically acceptable carriers of their own (WO01/35941).
5) A core formulation comprising (a) a first layer containing pioglitazone hydrochloride or a pharmaceutically acceptable salt thereof as an active ingredient, and (b) a core containing a biguanide as an active ingredient, wherein at least a portion of the core is enclosed by said first layer (WO01/82875).
6) a composition for treating diabetes, which contains an insulin sensitizer and an antidiabetic agent (U.S. Pat. No. 6,153,632, WO02/04024).

DISCLOSURE OF THE INVENTION

The present invention aims at providing a solid preparation comprising an insulin sensitizer and an active ingredient (except insulin sensitizers), which is useful as a therapeutic drug for diabetes and the like. and which is superior in preparation characteristics such as content uniformity and dissolution property of the insulin sensitizer and the active ingredient (except insulin sensitizers), preparation hardness and the like.

The present inventors have found that a solid preparation superior in content uniformity of insulin sensitizer and preparation hardness can be obtained by, when producing a solid preparation containing an insulin sensitizer and an active ingredient (except insulin sensitizers), uniformly dispersing both components. The present inventors have further studied based on this finding and, as a result, completed the present invention.

That is, the present invention relates to
1) a solid preparation having a phase wherein an insulin sensitizer and an active ingredient (except insulin sensitizers) are uniformly dispersed, and a hardness of 100 to 400N;
2) the solid preparation of the aforementioned 1), wherein the active ingredient is a biguanide;
3) the solid preparation of the aforementioned 2), wherein the biguanide is metformin hydrochloride;
4) a solid preparation having a phase wherein an insulin sensitizer and an active ingredient (except insulin sensitizers) having a ratio of median size thereof to the median size of said insulin sensitizer of 0.5 to 15 are uniformly dispersed;
5) the solid preparation of the aforementioned 4), wherein the active ingredient is a biguanide;
6) the solid preparation of the aforementioned 5), wherein the biguanide is metformin hydrochloride;
7) a solid preparation having a phase wherein an insulin sensitizer and an active ingredient (except insulin sensitizers) are uniformly dispersed, and a coefficient of variation of the insulin sensitizer content of not more than 6%;
8) the solid preparation of the aforementioned 7), wherein the active ingredient is a biguanide;
9) the solid preparation of the aforementioned 8), wherein the biguanide is metformin hydrochloride;
10) a solid preparation having a phase wherein an insulin sensitizer and an active ingredient (except insulin sensitizers) are uniformly dispersed, which elutes out not less than 70% of the insulin sensitizer at 30 min after in a dissolution test according to a Paddle Method using a hydrochloric acid-potassium chloride buffer (pH 2.0) as a test solution at 37° C., 50 rpm;
11) the solid preparation of the aforementioned 10), wherein the active ingredient is a biguanide;
12) the solid preparation of the aforementioned 11), wherein the biguanide is metformin hydrochloride;
13) a solid preparation having a phase wherein pioglitazone hydrochloride and metformin hydrochloride having a ratio of median size thereof to the median size of said pioglitazone hydrochloride of 0.5 to 15 are uniformly dispersed;
14) the solid preparation of the aforementioned 13), which is film-coated; and the like.

The insulin sensitizer to be used in the present invention may be any pharmaceutical agent as long as it restores damaged insulin receptor function and improves insulin resistance. As specific examples of the insulin sensitizer, the following compounds and salts thereof can be mentioned:
5-[4-[2-(5-ethyl-2-pyridyl)ethoxy]benzyl]-2,4-thiazolidinedione (general name: pioglitazone);
5-[[4-[2-(methyl-2-pyridinylamino)ethoxy]phenyl]methyl]-2,4-thiazolidinedione (general name: rosiglitazone);
5-[[6-(2-fluorobenzyloxy)-2-naphthyl]methyl]-2,4-thiazolidinedione (general name: netoglitazone);
5-(2,4-dioxothiazolidin-5-ylmethyl)-2-methoxy-N-[4-(trifluoromethyl)benzyl]benzamide (KRP-297);
4-[4-[2-(5-methyl-2-phenyloxazol-4-yl)ethoxy]benzyl]isoxazolidine-3,5-dione (JTT-501); FK-614; Tesaglitazar (AZ-242); Ragaglitazar (NN-622); BMS-298585; ONO-5816; CS-011; BM-13-1258; LM-4156; MBX-102; LY-519818; MX-6054; LY-510929; and (E)-4-[4-(5-methyl-2-phenyl-4-oxazolylmethoxy)benzyloxyimino]-4-phenylbutyric acid.

As the salt of the above-mentioned compound, pharmacologically acceptable salts such as salts with inorganic base, salts with organic base, salts with inorganic acid, salts with organic acid, salts with basic or acidic amino acid and the like can be mentioned.

As preferable examples of the salts with inorganic base, for example, salts with alkali metals (e.g. sodium, potassium and the like), alkaline earth metals (e.g. calcium, magnesium and the like), aluminum, ammonium and the like can be mentioned.

As preferable examples of the salts with organic base, for example, salts with trimethylamine, triethylamine, pyridine, picoline, ethanolamine, diethanolamine, triethanolamine, dicyclohexylamine, N,N-dibenzylethylenediamine and the like can be mentioned.

As preferable examples of the salts with inorganic acid, for example, salts with hydrochloric acid, hydrobromic acid, nitric acid, sulfuric acid, phosphoric acid and the like can be mentioned.

As preferable examples of the salts with organic acid, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like can be mentioned.

As preferable examples of the salts with basic amino acid, for example, salts with arginine, lysine, ornithine and the like can be mentioned, and as preferable examples of the salts with acidic amino acid, for example, salts with aspartic acid, glutamic acid and the like can be mentioned.

The insulin sensitizer is preferably pioglitazone hydrochloride, rosiglitazone maleate and the like, and particularly preferably pioglitazone hydrochloride.

In the present invention, two or more kinds of the insulin sensitizers may be used at an appropriate ratio.

The median size of the insulin sensitizer is preferably 1-100 μm, more preferably 1-70 μm. Particulraly, when the insulin sensitizer is pioglitazone hydrochloride, the median size of pioglitazone hydrochloride is preferably 1-25 μm, more preferably 2-21 μm. Particularly, by the use of pioglitazone hydrochloride having a median size of 2 to 10 μm, a solid preparation superior in dissolution property of pioglitazone hydrochloride can be obtained.

The above-mentioned preferable median size is applied to an insulin sensitizer used as a starting material (including a pulverized product obtained by pulverizing, a mixed pulverized product obtained by pulverizing together with an excipient, and the like during the production process of a solid preparation) for producing the solid preparation of the present invention. In other words, the median size of an insulin sensitizer may have changed due to the coagulation of insulin sensitizer and the like, during the production process of the solid preparation of the present invention, or during the process of preserving the solid preparation after production.

In the present specification, by the median size is meant a particle size that divides crude particles from fine granules at 50% each in weight distribution or number distribution. The median size can be measured using, for example, a known measurement device such as a laser diffraction particle distribution apparatus (e.g., HELOS&RODOS (trade name, manufactured by SYMPATEC GmbH) and the like.

As the insulin sensitizer having a desired median size mentioned above, for example, a commercially available product can be used. In addition, the insulin sensitizer having a desired median size can be also produced by pulverizing an insulin sensitizer having a large median size together with an excipient such as microcrystalline cellulose and the like as necessary. Here, the pulverization is performed according to a known method using, for example, a cutter mill, a hammer mill, a jet mill and the like.

In particular, when a solid preparation is produced using an insulin sensitizer having a weak binding force and a comparatively large median size, use of a large amount of additives such as a binder and the like, and the like may be designed to achieve sufficient preparation hardness. However, by making the median size of an insulin sensitizer smaller, a large amount of additives such as a binder and the like becomes unnecessary, which makes it possible to increase the drug content of a solid preparation.

As for the insulin sensitizer having a desired median size mentioned above, the dispersibility thereof is preferably such that "particles of not more than 0.1 μm are contained at not more than 10% of the total amount, and particles of not less than 1000 μm are contained at not more than 10% of the total amount".

As the active ingredient (except insulin sensitizers) to be used in the present invention, therapeutic agents for diabetes, therapeutic agents for diabetic complications, therapeutic agents for hyperlipidemia, antihypertensive agents, antiobesity agents, diuretics, antithrombotic agents and the like can be mentioned. These active ingredients may be a low-molecular-weight compound, a high-molecular-weight protein, polypeptide or antibody, a vaccine and the like. The active ingredient may be a mixture of two or more kinds of components at an appropriate ratio.

Examples of the therapeutic agents for diabetes include insulin preparations (e.g., animal insulin preparations extracted from the pancreas of bovine, swine; human insulin preparations synthesized by genetic engineering techniques using *Escherichia coli* or yeast; zinc insulin; protamine zinc insulin; fragments or derivatives of insulin (e.g., INS-1 etc.) and the like), α-glucosidase inhibitors (e.g., voglibose, acarbose, miglitol, emiglitate etc.), biguanide (e.g., phenformin, metformin, buformin, or a salt thereof (e.g., hydrochloride, fumarate, succinate) etc.), insulin secretagogues [sulfonylureas (e.g., tolbutamide, glibenclamide, gliclazide, chlorpropamide, tolazamide, acetohexamide, glyclopyramide, glimepiride, glipizide, glybuzole etc.), repaglinide, nateglinide, mitiglinide or calcium salt hydrate thereof, GLP-1 etc.], dipeptidylpeptidase IV inhibitors (e.g., NVP-DPP-278, PT-100, NVP-DDP-728, LAF237, etc.), β3 agonists (e.g., CL-316243, SR-58611-A, UL-TG-307, SB-226552, AJ-9677, BMS-196085, AZ-40140 etc.), amylin agonists (e.g., pramlintide etc.), phosphotyrosine phosphatase inhibitors (e.g., vanadic acid etc.), gluconeogenesis inhibitors (e.g., glycogen phosphorylase inhibitors, glucose-6-phosphatase inhibitors, glucagon antagonists etc.) and SGLUT (sodium-glucose cotransporter) inhibitors (e.g., T-1095 etc.).

Examples of the therapeutic agents for diabetic complications include aldose reductase inhibitors (e.g., tolrestat, epalrestat, zenarestat, zopolrestat, minalrestat, fidarestat (SNK-860), CT-112 etc.), neurotrophic factors (e.g., NGF, NT-3, BDNF etc.), neurotrophin production-secretion promoters [e.g., neurotrophin production-secretion promoters described in WO01/14372 (e.g., 4-(4-chlorophenyl)-2-(2-methyl-1-imidazolyl)-5-(3-(2-methylphenoxy)propyl)oxazole and the like)], PKC inhibitors (e.g., LY-333531 etc.), AGE inhibitors (e.g., ALT946, pimagedine, pyratoxanthine, N-phenacylthiazolium bromide (ALT766), EXO-226 etc.), active oxygen scavengers (e.g., thioctic acid etc.) and cerebral vasodilators (e.g., tiapride, mexiletine etc.).

Examples of the therapeutic agents for hyperlipidemia include HMG-CoA reductase inhibitors (e.g., pravastatin, simvastatin, lovastatin, atorvastatin, fluvastatin, lipantil, cerivastatin, itavastatin, ZD-4522, or their salts (e.g., sodium salts, calcium salts, etc.), etc.), fibrate compounds (e.g., bezafibrate, beclofibrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate etc.), squalene synthase inhibitors (e.g., compounds described in WO97/10224 (e.g., 1-[[(3R,5S)-1-(3-acetoxy-2,2-dimethylpropyl)-7-chloro-5-(2,3-dimethoxyphenyl)-2-oxo-1,2,3,5-tetrahydro-4,1-benzooxazepin-3-yl]acetyl]piperidine-4-acetic acid, etc.), ACAT inhibitors (e.g., Avasimibe, Eflucimibe etc.), anion exchange resins (e.g., colestyramine etc.), probucol, nicotinic acid drugs (e.g., nicomol, niceritrol etc.), ethyl icosapentate, plant sterols (e.g., soysterol, γ-oryzanol etc.) and the like.

Examples of the antihypertensive agents include angiotensin converting enzyme inhibitors (e.g., captopril, enalapril, delapril etc.), angiotensin II antagonists (e.g., candesartan cilexetil, losartan, eprosartan, valsartan, telmisartan, irbesartan, tasosartan etc.), calcium antagonists (e.g., manidipine, nifedipine, nicardipine, amlodipine, efonidipine etc.), potassium channel openers (e.g., levcromakalim, L-27152, AL 0671, NIP-121 etc.), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex etc.), pancreatic lipase inhibitors (e.g., orlistat etc.), β3 agonists (e.g., CL-316243, SR-58611-A, UL-TG-307, SB-226552, AJ-9677, BMS-196085, AZ-40140 etc.), peptidic anorexiants (e.g., leptin, CNTF (Ciliary Neurotropic Factor) etc.), cholecystokinin agonists (e.g., lintitript, FPL-15849 etc.) and the like.

Examples of the diuretics include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide etc.), chlorobenzenesulfonamide preparations (e.g., chlortalidone, mefruside, indapamide etc.), azosemide, isosorbide, etacrynic acid, piretanide, bumetanide, furosemide and the like.

Examples of the antithrombotic agents include heparin (e.g., heparin sodium, heparin calcium, dalteparin sodium etc.), warfarin (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

The active ingredient (except insulin sensitizers) to be used in the present invention is preferably a therapeutic agent for diabetes, more preferably a biguanide and a sulfonylurea, particularly preferably metformin or a salt thereof (preferably metformin hydrochloride).

The median size of the active ingredient (except insulin sensitizers) is preferably 0.5 to 1000 μm, more preferably 1 to 200 μm. Particularly, when the active ingredient is a biguanide (preferably metformin hydrochloride), the median size of the biguanide (preferably metformin hydrochloride) is preferably 10 to 100 μm, more preferably 10 to 80 μm.

The above-mentioned preferable median size is applied to an active ingredient (except insulin sensitizers) used as a starting material (including a pulverized product obtained by pulverizing, a mixed pulverized product obtained by pulverizing together with an excipient, and the like, during the production process of a solid preparation) for producing the solid preparation of the present invention. In other words, the median size of an active ingredient may have changed due to the coagulation of the active ingredient and the like, during the production process of the solid preparation of the present invention, or during the process of preserving the solid preparation after production.

As the active ingredient (except insulin sensitizers) having a desired median size mentioned above, for example, a commercially available product can be used. In addition, the active ingredient having a desired median size can be also produced by pulverizing an active ingredient having a large median size. Here, the pulverization is performed according to a known method using, for example, a cutter mill, a hammer mill, a jet mill and the like.

In particular, when a solid preparation is produced using an active ingredient having a weak binding force and a comparatively large median size, use of a large amount of additives such as a binder and the like, and the like may be designed to achieve sufficient preparation hardness. However, by making the median size of an active ingredient smaller, a large amount of additives such as a binder and the like becomes unnecessary, which makes it possible to increase the drug content of the solid preparation.

As for the active ingredient (except insulin sensitizers) having a desired median size mentioned above, the dispersibility thereof is preferably such that "particles of not more than 0.1 μm are contained at not more than 1% of the total amount, and particles of not less than 3000 μm are contained at not more than 10% of the total amount".

The ratio of the median size of the aforementioned active ingredient (except insulin sensitizers) to the median size of the aforementioned insulin sensitizer is preferably 0.5 to 15, more preferably 0.5 to 10.

By employing such ratio of the median size, the insulin sensitizer and the active ingredient can be dispersed more uniformly.

The above-mentioned preferable ratio is applied to an insulin sensitizer and an active ingredient used as a starting material (including a pulverized product obtained by pulverizing, a mixed pulverized product obtained by pulverizing together with an excipient, and the like, during the production process of a solid preparation) for producing the solid preparation of the present invention. In other words, the above-mentioned preferable ratio may have changed during the production process of the solid preparation of the present invention, or during the process of preserving the solid preparation after production.

The most preferable combination of an insulin sensitizer and an active ingredient (except insulin sensitizers) in the solid preparation of the present invention is that of pioglitazone hydrochloride and metformin hydrochloride.

The solid preparation of the present invention has a phase (part) wherein an insulin sensitizer and an active ingredient (except insulin sensitizers) are uniformly dispersed.

That is, the solid preparation of the present invention may be a preparation wherein an insulin sensitizer and an active ingredient (except insulin sensitizers) are uniformly dispersed in the entirety of the preparation, or may be a preparation partially containing such preparation, such as a coated preparation obtained by coating a preparation wherein an insulin sensitizer and an active ingredient (except insulin sensitizers) are uniformly dispersed in the entirety of the preparation, and the like.

In the present invention, as a dosage form of a solid preparation, for example, tablet, capsule, granule, powder, troche and the like can be mentioned. The dosage form of a solid preparation is preferably tablet. Furthermore, the shape of the solid preparation may be any such as round, caplet, oblong and the like. When the weight of the solid preparation is large, the shapes of caplet and oblong are preferable from the aspect of easy administration.

The solid preparation of the present invention may contain an additive conventionally used for the technical field of formulation of preparations. As such additive, for example, excipient, disintegrant, binder, lubricant, coloring agent, pH adjusting agent, surfactant, stabilizer, acidulant, flavor, glidant and the like can be mentioned. These additives are used in the amounts conventionally employed in the technical field of formulation of preparations.

As the excipient, for example, starches such as cornstarch, potato starch, wheat starch, rice starch, partly pregelatinized starch, pregelatinized starch, porous starch and the like; sugars and sugar alcohols such as lactose, fructose, glucose, mannitol, sorbitol and the like; anhydrous calcium phosphate, microcrystalline cellulose, precipitated calcium carbonate, calcium silicate and the like can be mentioned.

As the disintegrant, for example, carboxymethyl cellulose, calcium carboxymethyl cellulose, sodium carboxymethyl starch; croscarmellose sodium, crospovidone, low-substituted hydroxypropyl cellulose, hydroxypropyl starch and the like are used. The amount of the disintegrant to be used is preferably 0.5-25 parts by weight, more preferably 1-15 parts by weight, per 100 parts by weight of the solid preparation.

As the binder, for example, hydroxypropyl cellulose, hydroxypropylmethyl cellulose, polyvinylpyrrolidone, gum arabic powder and the like can be mentioned. The amount of the binder to be used is preferably 0.1-50 parts by weight, more preferably 0.5-40 parts by weight, per 100 parts by weight of the solid preparation. The binder is preferably hydroxypropyl cellulose or polyvinylpyrrolidone. Particularly, when the active ingredient to be used in the present invention is metformin hydrochloride, polyvinylpyrrolidone is preferable.

Preferable examples of the lubricant include magnesium stearate, calcium stearate, talc, sucrose esters of fatty acids, sodium stearyl fumarate and the like.

As the coloring agent, for example, food colors such as Food Yellow No. 5, Food Red No. 2, Food Blue No. 2 and the like, food lake colors, diiron trioxide and the like can be mentioned.

As the pH adjusting agent, citrate, phosphate, carbonate, tartrate, fumarate, acetate, amino acid salt and the like can be mentioned.

As the surfactant, sodium lauryl sulfate, polysorbate 80, polyoxyethylene (160) polyoxypropylene (30) glycol and the like can be mentioned.

As the stabilizer, for example, tocopherol, tetrasodium edetate, nicotinamide, cyclodextrins and the like can be mentioned.

As the acidulant, for example, ascorbic acid, citric acid, tartaric acid, malic acid and the like can be mentioned.

As the flavor, for example, menthol, peppermint oil, lemon oil, vanillin and the like can be mentioned.

As the glidant, for example, light silicic anhydride, hydrated silicon dioxide and the like can be mentioned. As used herein, light silicic anhydride may be any as long as it contains silicon dioxide hydrate ($SiO_2 \cdot nH_2O$) (n is an integer) as the main component, and as concrete examples thereof, Sylysia320 (trade name, Fuji Silysia Chemical Ltd.), AEROSIL200 (trade name, NIPPON AEROSIL CO., LTD.) and the like can be mentioned.

The above-mentioned additives may be used in a mixture of two or more kinds thereof at an appropriate ratio.

The insulin sensitizer content of the solid preparation of the present invention is, for example, 0.01-100 parts by weight, preferably 1-99 parts by weight, per 100 parts by weight of the solid preparation of the present invention.

Particularly, when the insulin sensitizer is pioglitazone hydrochloride, the pioglitazone hydrochloride content of the solid preparation of the present invention is, for example, preferably 0.01-15 parts by weight, more preferably 0.5-10 parts by weight, per 100 parts by weight of the solid preparation of the present invention.

The content of the active ingredient (except insulin sensitizers) in the solid preparation of the present invention is, for example, 0.1-100 parts by weight, preferably 1-99 parts by weight, per 100 parts by weight of the solid preparation of the present invention.

Particularly, when the active ingredient (except insulin sensitizers) is biguanide (preferably metformin hydrochloride), the biguanide (preferably metformin hydrochloride) content of the solid preparation of the present invention is, for example, preferably 5-98 parts by weight, more preferably 15-96 parts by weight, per 100 parts by weight of the solid preparation of the present invention.

The solid preparation of the present invention can be produced by, for example, uniformly mixing an insulin sensitizer and an active ingredient (except insulin sensitizers) with the aforementioned additives as necessary, or uniformly mixing after granulating, and then compression-molding.

Here, mixing is performed using, for example, a mixer such as a V-type mixer, a tumbler mixer and the like, and granulation is performed using, for example, a high speed mixer granulator, a fluid bed granulator-dryer and the like. For compression-molding, for example, punching is done generally at a pressure of 5-35 $kN/cm^2$ using a single punch tableting machine, a rotary tableting machine and the like.

For compression-molding using the aforementioned tableting machine, a tapered die is preferably used for preventing capping.

The solid preparation of the present invention is preferably produced by granulating an insulin sensitizer and an active ingredient (except insulin sensitizers) together with additives as necessary, such as excipient, glidant and the like, while spraying a solvent (e.g., water, ethanol) containing a binder (preferably polyvinylpyrrolidone when the active ingredient is metformin hydrochloride) dispersed or dissolved therein, drying the obtained granules, mixing the granules with additives such as excipient, disintegrant, lubricant and the like and then compression-molding the mixture.

A coated preparation can be also produced by coating a molded product obtained by compression-molding as mentioned above with a coating base.

As the coating base here, for example, a sugar coating base, a water-soluble film coating base, an enteric film coating base, a sustained-release film coating base and the like can be mentioned.

As the sugar coating base, sucrose is used, and one or more kinds selected from talc, precipitated calcium carbonate, gelatin, gum arabic, pullulan, carnauba wax and the like may be further used in combination.

As the water-soluble film coating base, for example, cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name), Rohm Pharma], polyvinylpyrrolidone etc.; polysaccharides such as pullulan etc.; and the like can be mentioned.

As the enteric film coating base, for example, cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name), Rohm Pharma], methacrylic acid copolymer LD [Eudragit L-30D55 (trade name), Rohm Pharma], methacrylic acid copolymer S [Eudragit S (trade name), Rohm Pharma] etc.; naturally occurring substances such as shellac etc.; and the like can be mentioned.

As the sustained-release film coating base, for example, cellulose polymers such as ethyl cellulose etc.; acrylic polymers such as aminoalkyl methacrylate copolymer RS [Eudragit RS (trade name), Rohm Pharma], ethyl acrylate-methyl methacrylate copolymer suspension [Eudragit NE (trade name), Rohm Pharma] etc.; and the like can be mentioned.

The aforementioned coating bases may be used after mixing with two or more kinds thereof at appropriately ratios. For coating, coating additives may be used.

As the coating additive, for example, light shielding agent and/or coloring agent such as titanium oxide, talc, diiron trioxide and the like; plasticizers such as polyethylene glycol, triethyl citrate, castor oil, polysorbates and the like; organic acids such as citric acid, tartaric acid, malic acid, ascorbic acid and the like; and the like can be mentioned.

The coating is performed according to known methods, for example, using a film coating equipment.

When a coated preparation is produced by coating the above-mentioned molded product, the proportion of the molded product is generally 70-99 parts by weight, preferably 90-98 parts by weight, per 100 parts by weight of the coated preparation.

In addition, a mark or a letter may be printed on the solid preparation of the present invention for identifiability, and a separating line may be made to facilitate division.

From the aspects of preparation strength and the like, the solid preparation of the present invention is preferably film coated.

The solid preparation of the present invention preferably has a hardness of 100 to 400N.

The solid preparation of the present invention preferably has a phase wherein an insulin sensitizer and an active ingredient (except insulin sensitizers), which has a ratio of median size thereof to the median size of said insulin sensitizer of 0.5 to 15 (preferably 0.5 to 10), are uniformly dispersed.

The above-mentioned preferable ratio is applied to an insulin sensitizer and an active ingredient used as a starting material (including a pulverized product obtained by pulverizing, a mixed pulverized product obtained by pulverizing together with an excipient, and the like, during the production process of a solid preparation) for producing the solid preparation of the present invention. In other words, the above-mentioned preferable ratio may have changed during the production process of the solid preparation of the present invention, or during the process of preserving the solid preparation after production.

The solid preparation of the present invention preferably shows a coefficient of variation of the insulin sensitizer content of not more than 6%. The coefficient of variation is preferably not more than 4%.

As used herein, the "coefficient of variation of the insulin sensitizer content" is a percentage (%) obtained by calculating the average value and the standard deviation of insulin sensitizer contents of plural solid preparations and dividing the standard deviation by the average value. The insulin sensitizer content of the solid preparation can be measured by known methods (e.g., liquid chromatography).

The solid preparation of the present invention preferably elutes out not less than 70% of the insulin sensitizer at 30 min after in a dissolution test according to a Paddle Method using a hydrochloric acid-potassium chloride buffer (pH 2.0) as a test solution at 37° C., 50 rpm.

Here, the dissolution test is performed according to a method described in the Japanese Pharmacopoeia 14th Edition. In addition, the "hydrochloric acid-potassium chloride buffer (pH 2.0)" to be used as a test solution can be prepared according to a known method. The amount of the hydrochloric acid-potassium chloride buffer to be used as a test solution is generally 900 mL.

The solid preparation of the present invention can be administered orally or parenterally and safely to mammals (e.g., mouse, rat, rabbit, cat, dog, bovine, horse, monkey, human and the like).

The solid preparation of the present invention and each component (e.g., insulin sensitizer such as pioglitazone hydrochloride and the like) in the solid preparation are useful as an agent for the prophylaxis or treatment of, for example, diabetes (e.g., type-1 diabetes, type-2 diabetes, gestational diabetes etc.), hyperlipidemia (e.g., hypertriglyceridemia, hypercholesterolemia, hypo-HDL-emia, postprandial hyperlipidemia etc.), impaired glucose tolerance [IGT (Impaired Glucose Tolerance)], diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection etc.), diabetic gangrene, xerostomia, hypacusis, cerebrovascular disorder, peripheral blood circulation disorder etc.], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease etc.), muscular dystrophy, myocardial infarction, angina pectoris, cerebrovascular accident (e.g., cerebral infarction, cerebral apoplexy), insulin resistance syndrome, Syndrome X, Dysmetabolic syndrome, hyperinsulinemia, hyperinsulinemia-induced sensory disorder, tumor (e.g., leukemia, breast cancer, prostate cancer, skin cancer etc.), irritable bowel syndrome, acute or chronic diarrhea, inflammatory diseases [e.g., Alzheimer's disease, chronic rheumatoid arthritis, spondylitis deformans, osteoarthritis, lumbago, gout, postoperative or traumatic inflammation, remission of tumentia, neuralgia, pharyngolaryngitis, cystitis, hepatitis (inclusive of nonalcoholic steatohepatitis), pneumonia, pancreatitis, inflammatory bowel disease, ulcerative colitis, etc.], visceral obesity syndrome, arteriosclerosis (e.g., atherosclerosis etc.) and the like.

The solid preparation of the present invention and each component (e.g., insulin sensitizer such as pioglitazone hydrochloride and the like) in the solid preparation are useful for the secondary prevention of various diseases mentioned above (e.g., secondary prevention of cardiovascular event such as cardiac infarction etc.) and suppression of progression (e.g., suppression of progression of impaired glucose tolerance into diabetes, suppression of progression of arteriosclerosis in diabetic patients).

The dose of the solid preparation of the present invention only needs to be an effective amount of an insulin sensitizer and an active ingredient (except insulin sensitizers) contained in the solid preparation.

The effective dose of the insulin sensitizer is, for example, generally 0.01-500 mg/day, preferably 0.1-100 mg/day, for an adult (body weight 60 kg).

Particularly, the effective amount of pioglitazone hydrochloride is generally 7.5-60 mg/day, preferably 15-60 mg/day, for an adult (body weight 60 kg), when the insulin sensitizer is pioglitazone hydrochloride.

When the insulin sensitizer is rosiglitazone malate, the effective amount of rosiglitazone malate is generally 1-12 mg/day, preferably 2-8 mg/day, for an adult (body weight 60 kg).

The effective amount of the active ingredient (except insulin sensitizers) is, for example, generally 0.01-10000 mg/day, preferably 0.1-5000 mg/day, for an adult (body weight 60 kg).

Particularly, the effective amount of a biguanide (preferably metformin hydrochloride) is generally 125-2550 mg/day, preferably 250-2550 mg/day, for an adult (body weight 60 kg), when the active ingredient is the biguanide (preferably metformin hydrochloride).

The frequency of the administration of the solid preparation of the present invention to the aforementioned mammals per day is preferably 1 or 2 times a day, more preferably once a day. Particularly, the solid preparation of the present invention is preferably administered once to a mammal before breakfast.

The solid preparation of the present invention may be used in combination with one or more pharmaceutical agents selected from therapeutic agents for diabetes, therapeutic agents for diabetic complications, therapeutic agents for hyperlipidemia, antihypertensive agents, antiobesity agents, diuretics, antithrombotic agents and the like (hereinafter sometimes to be abbreviated as a concomitant drug). As such concomitant drugs, those exemplified above as the active ingredient can be used. The time of administration of the solid preparation of the present invention and that of the concomitant drug are not limited, and they may be administered simultaneously or in a staggered manner to the administration subject. In addition, the solid preparation of the present invention and the concomitant drug may be administered to an administration subject as a single preparation containing them.

The dose of the concomitant drug can be appropriately determined based on the dose employed clinically. In addition, the mixing ratio of the solid preparation of the present invention and the concomitant drug can be appropriately determined according to the administration subject, administration route, target disease, condition, combination, and the like. For example, when the administration subject is a human, the concomitant drug may be used in an amount of 0.01 to 100 arts by weight per 1 part by weight of the solid reparation of the present invention.

Use of the concomitant drug in this way provides superior effects such as 1) enhancing the action of the solid preparation of the present invention or the concomitant drug (synergistic effect on the action of the pharmaceutical agents), 2) reducing the dose of the solid preparation of the present invention or the concomitant drug (effect of reducing the dose of pharmaceutical agents as compared to a single drug administration), 3) reducing the secondary action of the solid preparation of the present invention or the concomitant drug, and the like.

The present invention further provides "a production method of a solid preparation having a phase (part) wherein an insulin sensitizer and an active ingredient (except insulin sensitizers) are uniformly dispersed, which comprises fluidized bed-granulating the insulin sensitizer and the active ingredient (except insulin sensitizers) having a ratio of median size thereof to the median size of said insulin sensitizer of 0.5 to 15 (preferably 0.5 to 10).

Here, the fluidized bed granulating is performed according to a method known per se., for example, using a fluidized granulating dryer and the like. Where necessary, additives such as an excipient, a glidant, a binder and the like may be added during or before fluidized bed granulating. Alternatively, the granules obtained by fluidized bed granulating may be mixed with additives such as an excipient, a disintegrant, a lubricant and the like as necessary, and compression-olded, and the obtained molded product may be further coated with a coating base.

As used herein, as the additive and coating base, hose similar to the aforementioned can be used. In ddition, the compression-molding and coating are, erformed in the same manner as the above.

The production method of the present invention is useful for the production of a solid preparation containing a highly water-soluble active ingredient (e.g., metformin hydrochloride) as a convenient production method of a solid preparation superior in preparation characteristics such as content uniformity and dissolution property of the active ingredient and an insulin sensitizer, preparation hardness and the like.

The present invention is explained in detail in the following by referring to Examples, Reference Examples, Comparative Example and Experimental Examples, which are not to be construed as limitative.

In the following Examples and Comparative Example, the median size was measured by Helos & Rodos (trade name, manufactured by Sympatec). In the Examples, moreover, as various additives such as magnesium stearate and the like, the Japanese Pharmacopoeia 14th Edition compatible products were used.

Example 1

Metformin hydrochloride (median size: 29 μm, 267.6 g), pioglitazone hydrochloride (median size: 13 μm, 8.7 g) and cornstarch (4.2 g) were placed in a fluidized granulating dryer (manufactured by POWREX CORPORATION, LAB-1), granulated while spraying purified water (195 g) containing polyvinylpyrrolidone (19.5 g) and dried to give granules.

Microcrystalline cellulose (18.87 g), croscarmellose sodium (16.85 g) and magnesium stearate (1.35 g) were added to and mixed with the obtained granules.

The obtained powder mixture was tableted using a tableting machine (manufactured by Kikusui Seisakusho, Ltd., Correct12HUK) (tablet size: long diameter 13.5 mm×short diameter 8.5 mm, compression pressure: 9.6 kN/cm$^2$) to give tablets weighing 630 mg per tablet.

Example 2

Metformin hydrochloride (median size: 29 μm, 2283.1 g), pioglitazone hydrochloride (median size: 13 μm, 75.5 g), Sylysia320 (trade name, Fuji Silysia Chemical Ltd., 1.4 g), microcrystalline cellulose (85.7 g) were placed in a fluidized granulating dryer (manufactured by POWREX CORPORATION, FD-3SN), granulated while spraying purified water (1507 g) containing polyvinylpyrrolidone (150.7 g) and dried to give granules.

Microcrystalline cellulose (170 g), croscarmellose sodium (137.8 g) and magnesium stearate (9.1 g) were added to and mixed with the obtained granules.

The obtained powder mixture was tableted using a tableting machine (manufactured by Kikusui Seisakusho Ltd., Correct12HUK) (tablet size: long diameter 13.5 mm×short diameter 8.5 mm, compression pressure: 9.6 kN/cm$^2$) to give tablets weighing 638 mg per tablet.

The obtained tablets (1200 g) were cast in a film coating apparatus (Hicoater 30, manufactured by POWREX CORPORATION), and coating was performed by spraying a coating solution at an entrance temperature of 80° C. and at 2.0 g/min to give film-coated tablets weighing 657 mg per tablet. As the coating solution, a dispersion of hydroxypropylmethyl cellulose (22.0 g), polyethylene glycol 6000 (4.2 g), titanium oxide (4.2 g) and talc (4.2 g) in purified water (446 g) was used.

Example 3

Metformin hydrochloride (median size: 29 μm, 2318.2 g), pioglitazone hydrochloride (median size: 13 μm, 45.1 g), Sylysia320 (trade name, Fuji Silysia Chemical Ltd., 1.4 g) and microcrystalline cellulose (86.4 g) were placed in a fluidized granulating dryer (manufactured by POWREX CORPORATION, FD-3SN), granulated while spraying purified water (1500 g) containing polyvinylpyrrolidone (150 g) and dried to give granules.

Microcrystalline cellulose (170 g), croscarmellose sodium (138.2 g) and magnesium stearate (9.0 g) were added to and mixed with the obtained granules.

The obtained powder mixture was tableted using a tableting machine (manufactured by Kikusui Seisakusho Ltd., Correct12HUK) (tablet size: long diameter 17.5 mm×short diameter 9.5 mm, compression pressure: 11 kN/cm$^2$) to give tablets weighing 1070 mg per tablet.

The obtained tablets (1200 g) were cast in a film coating apparatus (Hicoater 30, manufactured by POWREX CORPORATION), and coating was performed by spraying a coating solution at an entrance temperature of 80° C. and at 2.0 g/min to give film-coated tablets weighing 1100 mg per tablet. As the coating solution, a dispersion of hydroxypropylmethyl cellulose (20.7 g), polyethylene glycol 6000 (4.0 g), titanium oxide (4.0 g) and talc (4.0 g) in purified water (327 g) was used.

Example 4

Metformin hydrochloride (median size: 29 μm, 2325.6 g), pioglitazone hydrochloride (median size: 13 μm, 38.4 g), Sylysia320 (trade name, Fuji Silysia Chemical Ltd., 1.4 g) and microcrystalline cellulose (88.1 g) were placed in a fluidized granulating dryer (manufactured by POWREX CORPORATION, FD-3SN), granulated while spraying purified water (1491 g) containing polyvinylpyrrolidone (149.1 g) and dried to give granules.

Microcrystalline cellulose (170 g), croscarmellose sodium (137.1 g) and magnesium stearate (8.8 g) were added to and mixed with the obtained granules.

The obtained powder mixture was tableted using a tableting machine (manufactured by Kikusui Seisakusho Ltd., Correct12HUK) (tablet size: long diameter 20.0 mm×short diameter 10.0 mm, compression pressure: 11 kN/cm$^2$) to give tablets weighing 1255 mg per tablet.

The obtained tablets (1200 g) were cast in a film coating apparatus (Hicoater 30, manufactured by POWREX CORPORATION), and coating was performed by spraying a coating solution at an entrance temperature of 80° C. and at 2.0 g/min to give film-coated tablets weighing 1290 mg per tablet. As the coating solution, a dispersion of hydroxypropylmethyl cellulose (20.8 g), polyethylene glycol 6000 (3.9 g), titanium oxide (3.9 g) and talc (3.9 g) in purified water (325 g) was used.

Example 5

Pioglitazone hydrochloride (median size: 13 μm) (10000 g) and microcrystalline cellulose (2500 g) were cast into a mixer (POWREX CORPORATION, vertical granulator) and mixed by stirring. The obtained mixture was pulverized in a jet mill pulverizer (NPK Co., Ltd., 100SP) to give a pulverized product (median size 3.6 μm) of a pioglitazone hydrochloride/microcrystalline cellulose mixture.

Metformin hydrochloride (median size: 29 μm, 4250 g), a pulverized product (median size 3.6 μm, 103.3 g) of a pioglitazone hydrochloride/microcrystalline cellulose mixture and microcrystalline cellulose (131.9 g) were cast in a fluidized granulating dryer (POWREX CORPORATION, FD-5S), granulated while spraying purified water (1375 g) containing polyvinylpyrrolidone (275 g), and dried to give granules.

Microcrystalline cellulose (320 g), croscarmellose sodium (253.4 g) and magnesium stearate (16.5 g) were added to and mixed with the obtained granules.

The obtained powder mixture was tableted using a tableting machine (manufactured by Kikusui Seisakusho Ltd., Correct12HUK) (tablet size: long diameter 17.5 mm×short diameter 9.5 mm, compression pressure: 20 kN/punch) equipped with a tapered die to give tablets weighing 1070 mg per tablet.

The obtained tablets (3600 g) were cast in a film coating apparatus (DRIACOATER500, manufactured by POWREX CORPORATION) and a coating solution was sprayed at an entrance temperature of 80° C. at 15.0 g/min to give film-coated tablets weighing 1100 mg per tablet. As the coating solution, a dispersion of hydroxypropylmethyl cellulose (63.8 g), polyethylene glycol 6000 (12.3 g), titanium oxide (12.3 g) and talc (12.3 g) in purified water (1000 g) was used.

Example 6

Pioglitazone hydrochloride (median size: 13 μm, 10000 g) and microcrystalline cellulose (2500 g) were cast into a mixer (POWREX CORPORATION, vertical granulator) and mixed by stirring. The obtained mixture was pulverized in a jet mill pulverizer (NPK Co., Ltd., 100SP) to give a pulverized product (median size 3.6 μm) of a pioglitazone hydrochloride/microcrystalline cellulose mixture.

Metformin hydrochloride (median size: 29 μm, 4500 g), a pulverized product (median size 3.6 μm, 185.9 g) of a pioglitazone hydrochloride/microcrystalline cellulose mixture and microcrystalline cellulose (127.5 g) were cast in a fluidized granulating dryer (POWREX CORPORATION, FD-5S), granulated while spraying purified water (1485 g) containing polyvinylpyrrolidone (297 g), and dried to give granules.

Microcrystalline cellulose (342 g), croscarmellose sodium (271.5 g) and magnesium stearate (18 g) were added to and mixed with the obtained granules.

The obtained powder mixture was tableted using a tableting machine (manufactured by Kikusui Seisakusho Ltd., Correct12HUK) (tablet size: long diameter 13.5 mm×short diameter 8.5 mm, compression pressure: 15 kN/punch) equipped with a tapered die to give tablets weighing 638 mg per tablet.

The obtained tablets (3600 g) were cast in a film coating apparatus (DRIACOATER500, manufactured by POWREX CORPORATION) and a coating solution was sprayed at an entrance temperature of 80° C. at 15.0 g/min to give film-coated tablets weighing 657 mg per tablet. As the coating solution, a dispersion of hydroxypropylmethyl cellulose (67.4 g), polyethylene glycol 6000 (13 g), titanium oxide (13 g) and talc (13 g) in purified water (1064 g) was used.

Reference Example 1

[Production of Coating Agent]

Hydroxypropylmethyl cellulose 2910 (TC-5) (350.4 g) and polyethylene glycol 6000 (72 g) were dissolved in purified water (4320 g). Titanium oxide (48 g) and yellow diiron trioxide (9.6 g) were dispersed in the obtained solution to give a coating agent.

[Production of Naked Tablet]

(E)-4-[4-(5-Methyl-2-phenyl-4-oxazolylmethoxy)benzyloxyimino]-4-phenylbutyric acid (hereinafter to be abbreviated as Compound A, 1184 g), lactose (1991 g), cornstarch (366.3 g) and croscarmellose sodium (233.9 g) were placed in a fluidized bed granulator dryer (manufactured by POWREX CORPORATION), preheated, mixed and granulated while spraying an aqueous solution (2591 g) containing hydroxypropyl cellulose (142.5 g). The obtained granule powder (3696 g) was passed through a power mill (manufactured by Showa Chemical Machinery Engineering) to give a sized powder. The obtained sized powder (3485 g), cornstarch (127.1 g) and magnesium stearate (18.15 g) were mixed in a tumbler mixer (manufactured by Showa chemical machinery engineering) and the obtained mixed powder was tableted by a tableting machine (manufactured by Kikusui Seisakusho Ltd.) to give naked tablets.

[Production of Film-Coated Tablet]

The aforementioned coating agent was sprayed on the obtained 24000 naked tablets in a film coating machine (manufactured by POWREX CORPORATION) to give film-coated tablets (24000 tablets) containing 32.0 mg of Compound A per tablet and having the following formulation.

Tablet Formulation (Composition per Tablet):
(Naked Tablet)

| 1) | Compound A | 32.0 mg |
| 2) | lactose | 53.8 mg |
| 3) | cornstarch | 13.75 mg |
| 4) | croscarmellose sodium | 6.05 mg |
| 5) | hydroxypropyl cellulose | 3.85 mg |
| 6) | magnesium stearate | 0.55 mg |
| | total | 110.0 mg |

(Film Components)

| 7) | hydroxypropylmethyl cellulose 2910 | 2.92 mg |
| 8) | polyethylene glycol 6000 | 0.6 mg |
| 9) | titanium oxide | 0.4 mg |
| 10) | yellow diiron trioxide | 0.08 mg |
| | total | 114.0 mg |

Reference Example 2

[Production of Coating Agent]

Hydroxypropylmethyl cellulose 2910 (TC-5) (101.9 g) and polyethylene glycol 6000 (20.4 g) were dissolved in purified water (1224 g). Titanium oxide (13.6 g) and yellow diiron trioxide (0.136 g) were dispersed in the obtained solution to give a coating agent.

[Production of Naked Tablet]

In the same manner as in Reference Example 1, a mixed powder was prepared and the obtained mixed powder was tableted by a tableting machine (Kikusui Seisakusho Ltd.) to give naked tablets.

[Production of Film-Coated Tablet]

The aforementioned coating agent was sprayed on the obtained 600 naked tablets in a film coating machine (manufactured by Freund Corporation) to give film-coated tablets (600 tablets) containing 48.0 mg of Compound A per tablet and having the following formulation.

Tablet Formulation (Composition per Tablet):
(Naked Tablet)

| 1) | Compound A | 48.0 mg |
| 2) | lactose | 80.7 mg |
| 3) | cornstarch | 20.625 mg |
| 4) | croscarmellose sodium | 9.075 mg |
| 5) | hydroxypropyl cellulose | 5.775 mg |
| 6) | magnesium stearate | 0.825 mg |
| | total | 165.0 mg |

(Film Components)

| 7) | hydroxypropylmethyl cellulose 2910 | 4.494 mg |
| 8) | polyethylene glycol 6000 | 0.9 mg |
| 9) | titanium oxide | 0.6 mg |
| 10) | yellow diiron trioxide | 0.006 mg |
| | total | 171.0 mg |

Reference Example 3

[Production of Coating Agent]

Hydroxypropylmethyl cellulose 2910 (TC-5) (101.2 g) and polyethylene glycol 6000 (20.4 g) were dissolved in purified water (1224 g). Titanium oxide (13.6 g) and yellow diiron trioxide (0.816 g) were dispersed in the obtained solution to give a coating agent.

[Production of Naked Tablet]

In the same manner as in Reference Example 1, a mixed powder was prepared and the obtained mixed powder was tableted by a tableting machine (Kikusui Seisakusho Ltd.) to give naked tablets.

[Production of Film-coated Tablet]

The aforementioned coating agent was sprayed on the obtained 320 naked tablets in a film coating machine (manufactured by Freund Corporation) to give film-coated tablets (320 tablets) containing 64.0 mg of Compound A per tablet and having the following formulation.

(Naked Tablet)

| 1) | Compound A | 64.0 mg |
| 2) | lactose | 107.6 mg |
| 3) | cornstarch | 27.5 mg |
| 4) | croscarmellose sodium | 12.1 mg |
| 5) | hydroxypropyl cellulose | 7.7 mg |
| 6) | magnesium stearate | 1.1 mg |
| | total | 220.0 mg |

(Film Components)

| 7) | hydroxypropylmethyl cellulose 2910 | 5.952 mg |
|---|---|---|
| 8) | polyethylene glycol 6000 | 1.2 mg |
| 9) | titanium oxide | 0.8 mg |
| 10) | yellow diiron trioxide | 0.048 mg |
| | total | 228.0 mg |

Reference Example 4

[Production of Coating Agent]
Hydroxypropylmethyl cellulose 2910 (TC-5) (298.8 g) and polyethylene glycol 6000 (60 g) were dissolved in purified water (3600 g). Titanium oxide (40 g) and yellow diiron trioxide (1.2 g) were dispersed in the obtained solution to give a coating agent.

[Production of Naked Tablet]
Compound A (1032 g), lactose (2657 g), cornstarch (425.7 g) and croscarmellose sodium (260.2 g) were placed in a fluidized bed granulator dryer (manufactured by POWREX CORPORATION), preheated, mixed and granulated while spraying an aqueous solution (2760 g) containing hydroxypropyl cellulose (165.6 g). The obtained granule powder (4277 g) was passed through a power mill (manufactured by Showa Chemical Machinery Engineering) to give a sized powder. The obtained sized powder (3696 g), cornstarch (134.8 g) and magnesium stearate (19.25 g) were mixed in a tumbler mixer (manufactured by Showa Chemical Machinery Engineering) and the obtained mixed powder was tableted by a tableting machine (Kikusui Seisakusho Ltd.) to give naked tablets.

[Production of Film-Coated Tablet]
The aforementioned coating agent was sprayed on the obtained 27000 naked tablets in a film coating machine (manufactured by POWREX CORPORATION) to give film-coated tablets (27000 tablets) containing 24.0 mg of Compound A per tablet and having the following formulation.

Tablet Formulation (Composition per Tablet):
(Naked Tablet)

| 1) | Compound A | 24.0 mg |
|---|---|---|
| 2) | lactose | 61.8 mg |
| 3) | cornstarch | 13.75 mg |
| 4) | croscarmellose sodium | 6.05 mg |
| 5) | hydroxypropyl cellulose | 3.85 mg |
| 6) | magnesium stearate | 0.55 mg |
| | total | 110.0 mg |

(Film Components)

| 7) | hydroxypropylmethyl cellulose 2910 | 2.988 mg |
|---|---|---|
| 8) | polyethylene glycol 6000 | 0.6 mg |
| 9) | titanium oxide | 0.4 mg |
| 10) | yellow diiron trioxide | 0.012 mg |
| | total | 114.0 mg |

Comparative Example 1

In the same manner as in Example 1 except that metformin hydrochloride (median size: 29 μm) was replaced by metformin hydrochloride (median size: 238 μm), tablets were obtained.

Experimental Example 1

The tablets obtained in the aforementioned Examples and Comparative Example were evaluated for content uniformity of these drugs by determining the coefficient of variation (%) of pioglitazone hydrochloride and metformin hydrochloride.

To be specific, the contents of pioglitazone hydrochloride and metformin hydrochloride in the tablets were measured by liquid chromatography, the average value and standard deviation of 3 tablets were determined, after which the standard deviation was divided by the average value and the percentage thereof was calculated. The results are shown in Table 1.

TABLE 1

Coefficient of variation (%) of pioglitazone hydrochloride and metformin hydrochloride

| | pioglitazone hydrochloride | metformin hydrochloride |
|---|---|---|
| Example 1 | 3.5 | 0.8 |
| Example 2 | 0.5 | 0.3 |
| Example 3 | 1.1 | 0.7 |
| Example 5 | 1.0 | 0.5 |
| Example 6 | 0.6 | 0.5 |
| Comparative Example 1 | 7.6 | 1.2 |

As shown in Table 1, the coefficient of variation of pioglitazone hydrochloride and metformin hydrochloride in the solid preparation of the present invention was small. In other words, the solid preparation of the present invention showed superior drug content uniformity.

Experimental Example 2

The tablets obtained in the aforementioned Examples and Comparative Example were measured for the tablet hardness in the long diameter direction using a tablet hardness meter (manufactured by Toyama Sangyo Co., Ltd.). The results are expressed in an average of 3 tablets. The results are shown in Table 2.

TABLE 2

Tablet hardness (N)

| | Tablet hardness (N) |
|---|---|
| Example 1 | 181 |
| Example 2 | 210 |
| Example 3 | 250 |
| Example 5 | 223 |
| Example 6 | 289 |
| Comparative Example 1 | 80 |

As shown in Table 2, the solid preparation of the present invention showed superior tablet hardness.

Experimental Example 3

The tablets obtained in the aforementioned Examples were evaluated for the dissolution property of pioglitazone hydrochloride by the Paddle Method (50 rpm) using a hydrochloric acid-potassium chloride buffer (900 mL, 37° C., pH 2.0). The results are shown in Table 3.

TABLE 3

| Dissolution rate (%) of pioglitazone hydrochloride | | | | |
|---|---|---|---|---|
| | time | | | |
| | 15 min | 30 min | 45 min | 60 min |
| Example 2 | 85.6 | 95.8 | 98.5 | 99.5 |
| Example 3 | 83.1 | 94.1 | 97.7 | 98.6 |
| Example 5 | 93.0 | 100.7 | — | — |
| Example 6 | 89.0 | 100.0 | — | — |

As shown in Table 3, the solid preparation of the present invention showed superior dissolution property of pioglitazone hydrochloride.

INDUSTRIALLY APPLICABILITY

The solid preparation of the present invention is useful as a therapeutic drug for diabetes and the like and is superior in preparation characteristics such as content uniformity and dissolution property of an insulin sensitizer and an active ingredient (except insulin sensitizers), preparation hardness and the like.

Moreover, the solid preparation of the present invention can be easily produced by a convenient method.

The invention claimed is:

1. A solid preparation comprising a phase, said phase comprising particles of pioglitazone or a salt thereof and particles of metformin or a salt thereof, wherein the particles of the pioglitazone or the salt thereof and the particles of the metformin or the salt thereof are uniformly dispersed particles, wherein the ratio of the median size of the particles of the metformin or the salt thereof to the median size of the particles of the pioglitazone or the salt thereof is 1 to 15, wherein the particles of the pioglitazone or the salt thereof have a median size of 2-10 μm, and the particles of the metformin or the salt thereof have a median size of 10-100 μm, and wherein an amount of the pioglitazone or the salt thereof in the preparation is 15-60 mg/day.

2. The solid preparation of claim 1, which is film-coated.

3. The solid preparation of claim 1, wherein pioglitazone or the salt thereof is pioglitazone hydrochloride.

4. The solid preparation of claim 1, wherein the metformin or the salt thereof is metformin hydrochloride.

5. The solid preparation of claim 1, wherein the pioglitazone or the salt thereof is pioglitazone hydrochloride and the metformin or the salt thereof is metformin hydrochloride.

6. The solid preparation of claim 1, wherein the solid preparation has a coefficient of variation of the pioglitazone or the salt thereof content of not more than 6%.

7. The solid preparation of claim 1, wherein the solid preparation has a hardness of 100 N to 400 N.

8. The solid preparation of claim 1, which elutes out not less than 70% of the pioglitazone or a salt thereof at 30 minutes after in a dissolution test according to a Paddle Method using a hydrochloric acid-potassium chloride buffer having pH of 2.0 as a test solution at 37° C., 50 rpm.

9. The solid preparation of claim 1, which is an agent for treatment of diabetes comprising an amount of the pioglitazone or salt thereof and an amount of the metformin or salt thereof effective for the treatment of diabetes.

10. The solid preparation of claim 1, wherein the amount of the pioglitazone or the salt thereof in the preparation is 15 mg/day.

11. The solid preparation of claim 1, wherein an amount of the metformin or the salt thereof in the preparation is 250-2550 mg/day.

12. The solid preparation of claim 1, wherein the pioglitazone or the salt thereof and the metformin or the salt thereof are sole active ingredients of the preparation.

13. A solid preparation comprising a phase, said phase comprising particles of pioglitazone or a salt thereof and particles of metformin or a salt thereof, wherein the particles of the pioglitazone or the salt thereof and the particles of the metformin or the salt thereof are uniformly dispersed, and wherein the ratio of the median size of the particles of the metformin or the salt thereof to the median size of the particles of the pioglitazone or the salt thereof is 1 to 15, and wherein
   (1) the particles of the pioglitazone or the salt thereof have a median size of 2-10 μm, and the particles of the metformin or the salt thereof have a median size of 10-100 μm,
   (2) the solid preparation has a coefficient of variation of the pioglitazone or the salt thereof content of not more than 6%,
   (3) the solid preparation has a hardness of 100 to 400N, and
   (4) the solid preparation elutes out not less than 70% of the pioglitazone or the salt thereof at 30 minutes after in a dissolution test according to a Paddle Method using a hydrochloric acid-potassium chloride buffer having a pH of 2.0 as a test solution at 37° C., 50 rpm, and wherein an amount of the pioglitazone or the salt thereof in the preparation is 15-60 mg/day.

14. The solid preparation of claim 13, wherein the amount of the pioglitazone or the salt thereof in the preparation is 15 mg/day.

15. The solid preparation of claim 13, wherein an amount of the metformin or the salt thereof in the preparation is 250-2550 mg/day.

16. The solid preparation of claim 13, wherein the pioglitazone or the salt thereof and the metformin or the salt thereof are sole active ingredients of the preparation.

* * * * *

UNITED STATES PATENT AND TRADEMARK OFFICE
CERTIFICATE OF CORRECTION

| | | Page 1 of 1 |
|---|---|---|
| PATENT NO. | : 9,101,660 B2 | |
| APPLICATION NO. | : 10/530262 | |
| DATED | : August 11, 2015 | |
| INVENTOR(S) | : Masahiko Koike et al. | |

It is certified that error appears in the above-identified patent and that said Letters Patent is hereby corrected as shown below:

In The Claims
Col. 19, claim 1, line 31, "are uniformly dispersed particles," should be --are uniformly dispersed,--.

Signed and Sealed this
Twenty-third Day of February, 2016

Michelle K. Lee
*Director of the United States Patent and Trademark Office*